US007295648B2

(12) United States Patent
Brown

(10) Patent No.: US 7,295,648 B2
(45) Date of Patent: Nov. 13, 2007

(54) METHOD AND APPARATUS FOR TREATMENT BY IONIZING RADIATION

(75) Inventor: Kevin John Brown, Horsham (GB)

(73) Assignee: Elektra AB (Publ), Stockholm (SE)

( * ) Notice: Subject to any disclaimer, the term of this patent is extended or adjusted under 35 U.S.C. 154(b) by 0 days.

(21) Appl. No.: 10/971,298

(22) Filed: Oct. 21, 2004

(65) Prior Publication Data

US 2005/0089141 A1    Apr. 28, 2005

(30) Foreign Application Priority Data

Oct. 23, 2003   (GB)   ................. 0324676.6
Nov. 4, 2003    (GB)   ................. 0325698.9

(51) Int. Cl.
*A61N 5/10* (2006.01)

(52) U.S. Cl. .................... 378/65; 378/17; 378/21; 378/193; 378/195; 378/196

(58) Field of Classification Search .............. 378/65; 250/492.3

See application file for complete search history.

(56) References Cited

U.S. PATENT DOCUMENTS

| 2,890,349 | A | * | 6/1959 | Huszar | .................. 378/65 |
| 3,777,124 | A | | 12/1973 | Pavkovich | |
| 4,741,015 | A | * | 4/1988 | Charrier | ............... 378/196 |

(Continued)

FOREIGN PATENT DOCUMENTS

DE    EP 0 248 774 A1   12/1987

(Continued)

OTHER PUBLICATIONS

Nakagawa, K. et al. "Intercomparison of Dose Distribution Between Gamma Knife and C-Arm-Mounted Linac". *Radiation Medicine*, Jul. 1-Aug. 1, 2003. pp. 178-182. vol. 21, No. 4. XP003042571. Japan.

Primary Examiner—Robert Kim
Assistant Examiner—James J Leybourne
(74) Attorney, Agent, or Firm—Kenneth L. Sherman, Esq.; Myers, Dawes, Andras & Sherman, LLP

(57) ABSTRACT

A radiation therapy/surgery device optimised to meet the needs of the Neurosurgeon is provided, i.e. one for the treatment of tumours in the brain. It combines the qualities of a good penumbra and accuracy, simple prescription and operation, together with high reliability and minimal technical support. The device comprises a rotateable support, on which is provided a mount extending from the support out of the plane of the circle, and a radiation source attached to the mount via a pivot, the pivot having an axis which passes through the axis of rotation of the support, the radiation source being aligned so as to produce a beam which passes through the co-incidence of the rotation axis and the pivot. It will generally be easier to engineer the apparatus if the rotateable support is planar, and more convenient if the rotateable support is disposed in an upright position. The rotation of the rotateable support will be eased if this part of the apparatus is circular. A particularly preferred orientation is one in which the radiation source is spaced from the rotateable support, to allow it to pivot without fouling the latter. It is thus preferred that the mount extends transverse to the support. In this way, the pivot axis is spaced from the rotateable support providing free space in which the radiation source can pivot. Another way of expressing this preference is to state that the pivot axis is located out of the plane of the rotateable support. To simplify the geometry of the device and the associated arithmetic, it is preferred both that the pivot axis is substantially perpendicular to the rotation axis, and that the beam direction is perpendicular to the pivot axis. It is preferred that the radiation source is a linear accelerator. The output of the radiation source is preferably collimated to conform to the shape of the area to be treated.

23 Claims, 16 Drawing Sheets

U.S. PATENT DOCUMENTS

| | | |
|---|---|---|
| 5,189,687 A * | 2/1993 | Bova et al. ................... 378/65 |
| 5,528,651 A | 6/1996 | Leksell et al. |
| 5,751,781 A * | 5/1998 | Brown et al. ................. 378/65 |
| 5,823,192 A * | 10/1998 | Kalend et al. ............. 128/845 |
| 6,309,102 B1 | 10/2001 | Stenfors |
| 7,062,007 B2 * | 6/2006 | Morita ........................ 378/17 |
| 7,085,347 B2 * | 8/2006 | Mihara et al. ................ 378/65 |
| 2004/0240621 A1 * | 12/2004 | Noguchi ..................... 378/150 |

FOREIGN PATENT DOCUMENTS

| | | |
|---|---|---|
| DE | 197 17 109 A1 | 4/1998 |
| WO | WO 96/18341 A1 | 6/1996 |
| WO | WO 03/018131 A1 | 3/2003 |

\* cited by examiner

METHOD AND APPARATUS FOR TREATMENT BY IONIZING RADIATION

FIELD OF THE INVENTION

This invention relates to a device for treating a patient with ionising radiation. It is particularly suited to forms of radiosurgery and to certain forms of radiotherapy.

BACKGROUND ART

It is known that exposure of human or animal tissue to ionising radiation will kill the cells thus exposed. This finds application in the treatment of pathological cells. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, resulting in prolonged recovery periods for the patient. It is, therefore, desirable to design a device for treating a patient with ionising radiation and treatment protocols so as to expose the pathological tissue to a dose of radiation, which will result in the death of these cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures from a single source. The intensity of radiation emanating from each source is therefore less than would be required to destroy cells, but where the radiation beams from the multiple sources converge, the intensity of radiation is sufficient to deliver a therapeutic dose.

The point of intersection of the multiple radiation beams is herein referred to as the "target point". The radiation field surrounding a target point is herein referred to as the "target volume", the size of which can be varied by varying the size of the intersecting beams.

A radiation device of this type is sold by the applicant as the Leksell Gamma Knife® (LGK). The LGK device is described in U.S. Pat. No. 4,780,898 and U.S. Pat. No. 5,528,651. In the LGK, a plurality of radiation sources are distributed around the head of the patient, in a hemispherical arrangement. By means of suitable collimators, the radiation beams from each source are focussed to a small volume in the brain. The LGK is commonly regarded as the 'gold standard' for delivering radiation to destroy pathological tissues in the brain, as a result of (i) the low background radiation away from the target volume as compared to the high radiation intensity within the target volume and (ii) the small dimensions of the target volume. This enables the surgeon to excise small areas accurately and swiftly, without damage to surrounding structures. An acknowledgement of the LGK appears at Nakagawa et al, Radiation Medicine, Vol 21, No. 4, pp 178-182, 2003.

The LGK uses Magnetic Resonance Imaging (MRI), Computer Tomography (CT), PET and/or angiography to determine the exact location of the tumour, with the patient being held in a fixed position by the use of a reference frame, to construct a three-dimensional image of the target. The treatment parameters for each radiation beam are then determined such that the pathological tissue is treated to the necessary dose of radiation, whilst surrounding healthy tissue receives a minimal dose of radiation.

The treatment may be spread over a number of days or weeks, thus requiring that the patient is placed in exactly the same position in relation to the point of intersection of the converging beams at each treatment, to avoid the risk that pathological tissue is missed or that surrounding healthy tissue is irradiated unintentionally. This is extremely important in the case where diseases in the brain are treated, which requires the radiation beam to be focussed with pinpoint accuracy to avoid damage to sensitive areas such as e.g. the optic nerve, which if irradiated will result in the patient losing their sight, even with only small doses. This method therefore calls for the presence of a highly skilled, specialist team of technical experts to provide radiation treatment using these appliances.

A modification of the LGK has been proposed in the form of U.S. Pat. No. 5,757,886 (Song), which involves placing cobalt sources in a ring configuration. A group of different collimators for each source are mounted on a hemispherical support that can be rotated relative to the sources to bring one collimator of the group into register, for each source. This allows a wider choice of collimators, at the expense of fewer cobalt sources and correspondingly greater treatment times.

Other forms of radiotherapy are delivered using linear-accelerator-based systems. A linear accelerator uses radio-frequency energy to create a varying magnetic & electrical field in a elongate accelerating chamber—hence a "linear" accelerator. Electrons are fed into the chamber and are accelerated to near light speed. The resulting beam can be used directly as a form of radiation, but it is more usual to direct this to a suitable "target", a block of an appropriate heavy metal such as tungsten. The electron beam impinges on the tungsten block and causes it to emit a beam of x-radiation. The geometry of the electron beam and the tungsten surface are arranged so that the x-ray beam departs perpendicular to the incoming electron beam and can thus be directed towards a patient.

The x-ray beam is collimated to a suitable shape and passes through the patient causing tissue damage. By suitable collimation and by moving the linear accelerator around the patient so that it approaches from a range of directions, such systems can minimise the dosage outside the tumour and maximise it within the tumour.

The principal disadvantage with linear accelerator systems is that the accelerator is extremely heavy. To combine the necessary electrical and thermal properties requires the accelerator chamber to be constructed of large copper blocks. The production of x-rays also produces unwanted radiation, which has to be attenuated by large amounts of shielding material e.g. Tungsten, and this combined with the other components required to operate the linear accelerator will cause the apparatus as a whole to be extremely heavy.

This weight must be supported, and the apparatus moved accurately so that the radiation beam can be directed towards the patient from a range of directions. For bodily tumours, the usual compromise is to mount the linear accelerator in an arm extending from a rotateable mount. The beam then exits from the end of the arm, directed inwardly towards the centreline of the mount. A patient supported at the intersection of the centreline and the beam can them be treated; as the mount rotates, the beam will meet the patient from a range of directions within the same plane.

Such systems are not generally used for tumours of the brain. They are too inflexible, as the beam must approach the patient from a direction that is within a single plane. If that plane includes a sensitive structure, such as the optic nerve, severe damage could be caused. In the LGK, for example, beams approach from all directions and the element that would interfere with such a structure can be blocked.

It is possible to mount a linear accelerator on a robotic arm, to allow a wide range of possible motions. Proposals of this type have been made, and these would, in theory, overcome this problem. However, the great weight of the linear accelerator structure means that it is extremely difficult to engineer such a robotic arm so that the movement is carried out with the precision required for tumours of the brain. Such tumours require placement accuracy of tens of thousandths of a inch or less, and to move an item weighing several tons at the end of an arm that may be several yards long to such levels of accuracy is a near impossible task. Thus, whilst such designs can be constructed and find application to bodily tumours, they are not sufficiently accurate for use with tumours of the brain.

Nakagawa et al, cited above, proposes a system of this type in which some flexibility of movement is sacrificed in favour of greater accuracy. The linear accelerator is mounted on one end of a C-arm, which is (in turn) held in a rotateable support. The C-arm can move on its support; thus at its two extremities of motion it resembles more a U-arm or an inverted U. As it moves, the angle of entry of the radiation beam will change. Thus, combined with rotation of the support, will give the necessary range of motion. However, as the C-arm moves, the centre of gravity of the apparatus will shift, causing errors. To counteract this, Nakagawa et al require a complex system of retractable balance weights in order to prevent movement; this is a potential weakness in the accuracy of the apparatus.

SUMMARY OF THE INVENTION

Cells (and the living tissue that they make up) respond to ionizing radiation in a very complex manner. The radiation sensitivity of cells depends on a number of factors including histology and (for instance) on their oxygenation. Anoxic cells, common in central parts of tumours, are relatively radiation resistant as compared to otherwise similar well-oxygenated cells. A second important biological factor is the repair of radiation damage induced in the DNA strands of cells. A radiation dose delivered over a relatively longer period of time causes less damage to DNA as when the same dose is given over a relatively short time. The cell has more time to repair during a longer exposure, and is thus given a better chance to survive. If cells of normal tissue survive as a result of longer exposures, healthy tissue may be spared. On the other hand, if the surviving cells are malignant they may continue to divide and the patient may not be cured.

Thus, an ideal irradiation apparatus will provide the largest possible freedom in the delivery of the radiation dose. The radiation must be delivered accurately and very selectively to small regions of delicate neurological and other tissue. This advanced irradiation procedure must be reproducible during the entire lifetime of the treatment unit.

It is an object of the invention to provide a radiation therapy and/or surgery device thus optimised to meet the needs of the Neurosurgeon, i.e. for the treatment of pathological tissue in the brain or vicinity. It combines the qualities of a good penumbra and accuracy, simple prescription and operation, together with high reliability and minimal technical support.

Preferred embodiments of the invention deliver radiation with high geometrical accuracy from a wide range of directions. The dose rate can be changed in a wide range with the irradiation direction. The cross section of the radiation beam can be changed in shape and size with irradiation direction.

The present invention therefore provides a device for treating a patient with ionising radiation comprising a support, on which is provided a mount, a radiation source attached to the mount, the support being rotateable about an axis, the source being attached to the mount via a rotateable union having an axis of rotation which is non-parallel to the support axis, wherein the axis of the mount passes through the axis of the support and the radiation source is collimated so as to produce a beam which passes through the co-incidence of those axes.

Patients generally prefer to lie down whilst being treated, and are more likely to remain still if doing so. It is therefore preferred that the rotateable support is disposed in an upright position.

The rotation of the rotateable support will be eased if this part of the apparatus is circular.

A preferred orientation is one in which the radiation source is spaced from the rotateable support, to allow it to pivot without fouling the latter. It is thus preferred that the mount extends transverse to the support. In this way, the pivot axis is spaced from the rotateable support providing free space in which the radiation source can pivot. Another way of expressing this preference is to state that the pivot axis is located out of the plane of the rotateable support.

To simplify the geometry of the device and the associated arithmetic, it is preferred both that the pivot axis is substantially perpendicular to the rotation axis, and that the beam direction is perpendicular to the pivot axis.

It is preferred that the radiation source is a linear accelerator.

The output of the radiation source is preferably collimated, for example to conform to the shape of the area to be treated. The degree of collimation of the radiation source is preferably selectable or adjustable. It is preferred that a control means is provided, for programmably controlling the collimation of the radiation source in a manner correlated with the movement thereof.

The apparatus will generally include a patient support. It is preferred that the position of the patient support is adjustable, particularly under the control of the control means, with the control means being adapted to adjust that position in a manner correlated with the movement of the radiation source and/or the collimation thereof. This will allow increased flexibility in treatment.

It is also preferred that the intensity of the radiation source is selectable as a function of its position. Again, it is preferable for this to be under the control of the control means, adapted to adjust that intensity in a manner correlated with at least one of the movement of the radiation source, the collimation thereof, and the position of a patient table.

An integral imaging device can be used to determine the position of the patient, for example by way of feedback to the control means.

BRIEF DESCRIPTION OF THE DRAWINGS

An embodiment of the present invention will now be described by way of example, with reference to the accompanying figures in which;

FIGS. 1a to 1c show the effect of rotation about the rotateable union, whereas FIGS. 2a to 2c show the effect of rotation of the support.

DETAILED DESCRIPTION OF THE EMBODIMENTS

Figure 1A:
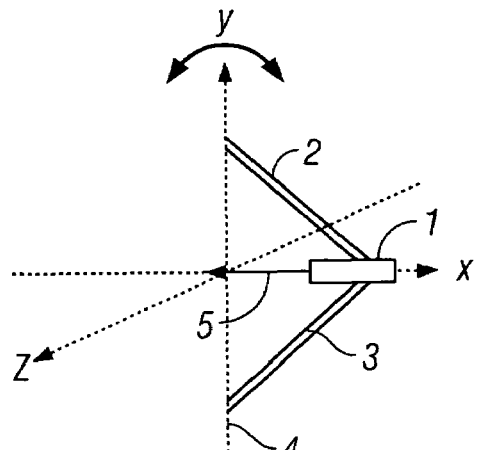
FIGS. 1a to 1c and FIGS. 2a to 2c show the geometrical arrangement of the apparatus, in schematic terms.
Figure 1B:
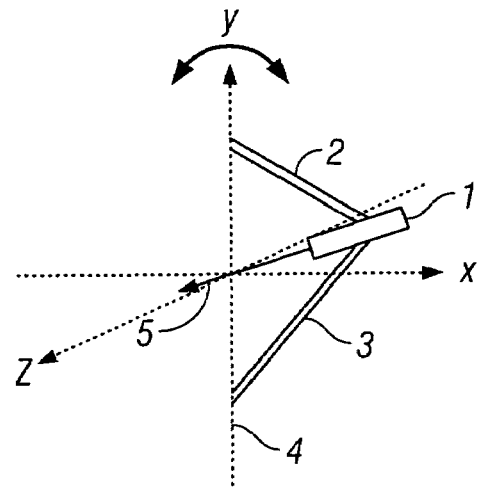
Figure 1C:
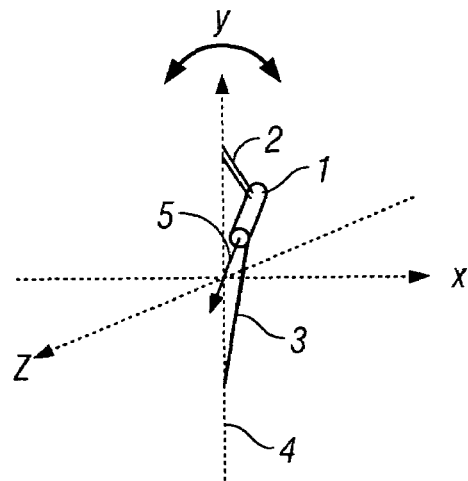
Figure 2A:
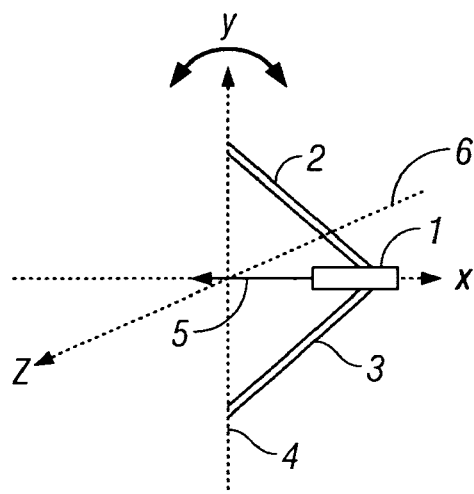
Figure 2B:
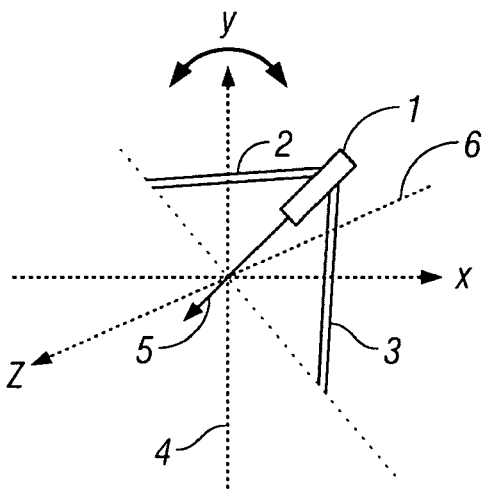
Figure 2C:
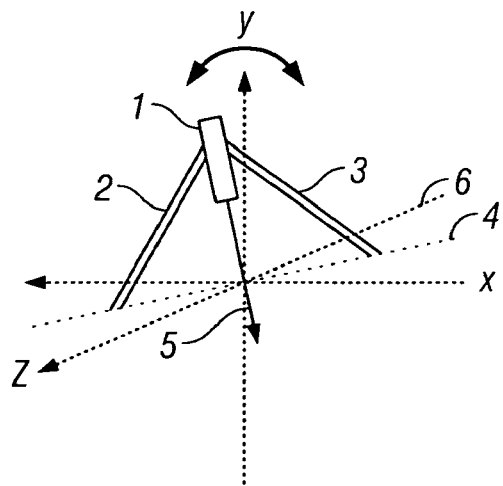

FIGS. 1a, 1b and 1c, together with FIGS. 2a, 2b and 2c, show the general principle of operation according to the present invention. They show that the geometry adopted by the invention constrains the radiation source such that a wide variety of approach angles are possible, but that the source can only point towards the isocentre.

Further, they illustrate how such an arrangement can be achieved using only rotateable joints. Thus, once the device is suitably supported or balanced around those joints, the problems inherent in the Nakagawa et al arrangement are avoided.

There are two main rotation axes according to the invention. FIGS. 1a, 1b and 1c show the effect of rotation about one of the axes, while FIGS. 2a, ab and 2c show the effect of rotation about the other. It is envisaged that, in practice, both axes would be used simultaneously.

FIG. 1a shows the device in a rest state in which a source 1 is supported by rigid members 2, 3 which are each attached to a base (not shown) so that they are rotateable about a vertical axis 4. In FIG. 1a, this axis coincides with the geometrical y axis. The specific shape of the members 2, 3 is not important to this explanation and they have therefore been shown as simple linear struts. The vertical axis 4 is offset from the source 1, whose output beam 5 points back towards the vertical axis. In its rest state, the beam points back along a line that can be adopted as the geometrical x axis, perpendicular to the y axis. The origin of the x and y axes is then the intersection of the vertical axis 4 and the beam 5, and is in fact the isocentre of the device (as will become apparent).

FIG. 1b shows the effect of a small rotation around the vertical axis 4. This takes the source and beam away from the geometrical x axis towards the geometrical z axis, shown in FIG. 1b perpendicular to the x and y axes. The vertical axis about which the rotation is taking place co-incides with the beam 5, with the result is that the beam 5 continues to intersect with the vertical axis 4 at the same point—the isocentre.

FIG. 1c then shows the effect of a still further rotation, taking the source 4 past the z axis and illustrating that the beam 5 continues to intersect with the vertical axis at the isocentre.

Referring to FIG. 2a, the effect of the second axis of rotation called for by the present invention will now be discussed. This rotation allows wholesale rotation of the support to which the rigid strut members 2, 3 are attached. Accordingly, rotation about this second axis 6 will take with it all the parts discussed above, including the formerly "vertical" axis 4. The axis 6 of this rotation co-incides with the geometrical z axis illustrated in the figures; as a result, that axis passes through the isocentre. FIG. 2a shows the device prior to any rotation, in the same rest state as FIG. 1a.

FIG. 2b shows a small rotation about the second axis 6. It should be noted that the first axis 4 is no longer co-incident with the geometrical y axis. Nevertheless, because the beam 5, "vertical" axis 4 and second axis 6 all co-incide at the isocentre, the beam continues to pass through the same isocentre despite this rotation.

FIG. 2c shows the effect of a further rotation about the second axis 6. It can be seen that the beam still passes through the isocentre.

As mentioned above, in practice both rotations will be used simultaneously. This will mean that, in principle, any direction of approach can be obtained. If the first axis 4 is fixed at an arbitrary rotation, then rotation about the second axis 6 will allow the beam to be directed towards the isocentre from any direction along a cone centred on the second axis; the angle at which the first axis is fixed will define the angle of the cone. Likewise, if the second axis 6 is fixed at an arbitrary rotation, then rotation about the first axis 4 will allow the beam to be directed towards the isocentre from any direction in the plane that includes the beam direction 5 and the second axis 6; the angle of that plane will be defined by the angle of rotation about the second axis.

Thus, the invention proposes the use of a source mounted so as to be rotateable about two axes, with both axes and the beam direction all being co-incident at a single isocentre. This allows a device to be constructed that is inherently accurate in that the source can only point towards the isocentre.

It will of course be apparent that the embodiment could be disposed in any suitable orientation, with the same geometrical result being obtained. Thus, in the above, whilst one axis has been referenced as being a "vertical" axis, this is only for reasons of clarity and does not infer that the specific directions are essential to operation of the device.

Figure 3:
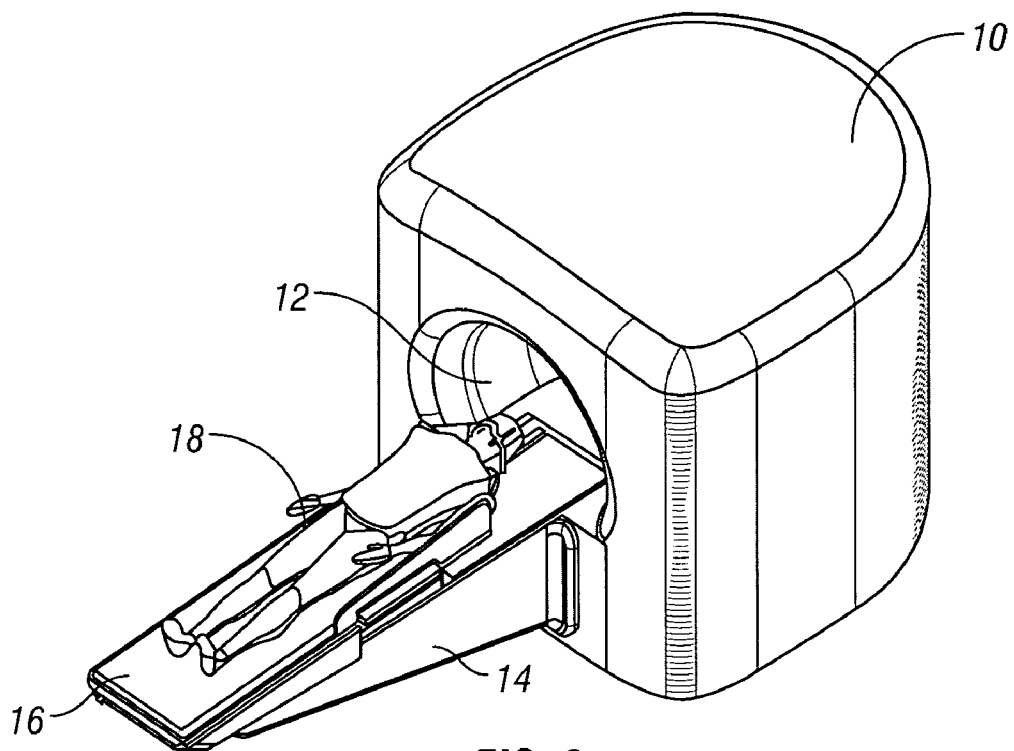
FIG. 3 shows an external view of the apparatus prior to insertion of a patient.

FIG. 3 shows the general external appearance of a device according to the present invention. The device 10 comprises an enclosure in which is formed a concave recess 12. Between the enclosure and the recess 12 is provided the apparatus for producing a therapeutic beam of radiation, to be described later. The material defining the concave enclosure 12 will be of a material that is radio-transparent so as to allow transmission of the therapeutic beam into the enclosure.

Figure 4:
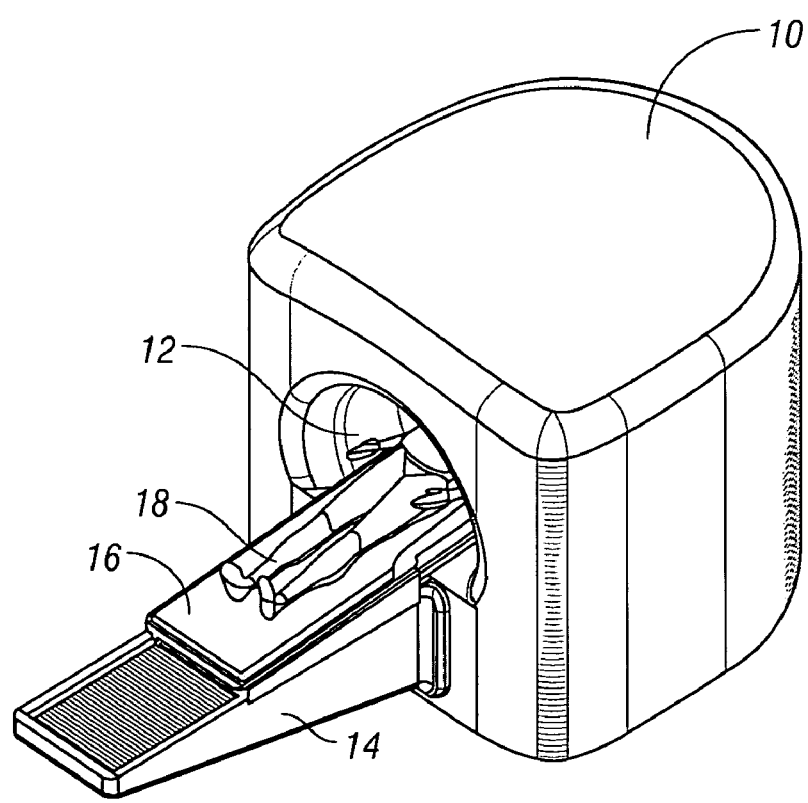
FIG. 4 shows the apparatus with the patient in a treatment position.

A patient table 14 is located outside the concave enclosure 12, on which is formed a moveable patient support 16. The patient 18 lies on the moveable support 16, which is then moved as shown in FIG. 4 to bring the patient inside the concave enclosure 12. In this position, the therapeutic beam of radiation can be directed at the relevant part of the patient 18.

Figure 5:
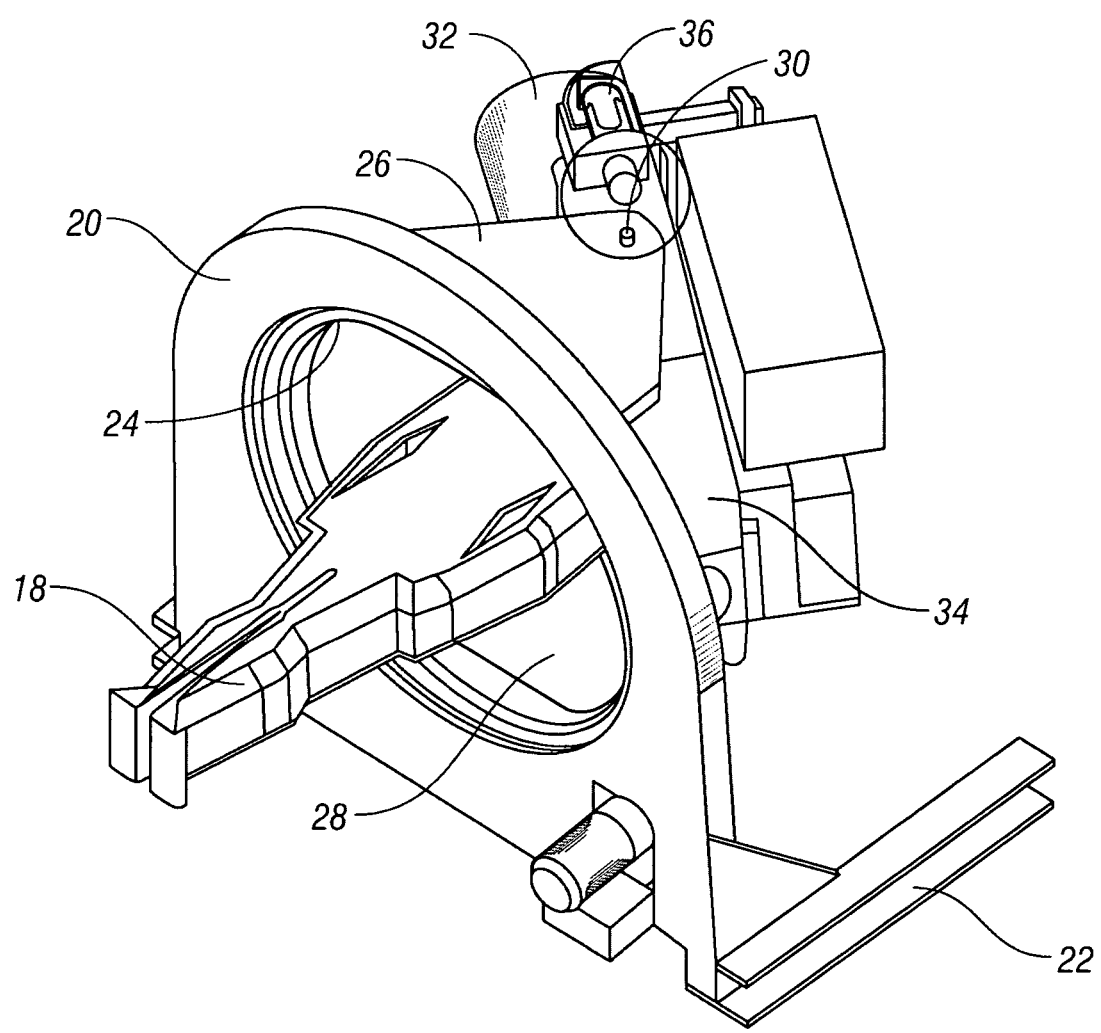
FIG. 5 shows a perspective view of the internal structure of the apparatus from a foot end.

FIG. 5 shows the interior workings of the apparatus, ie. with the patient table and all exterior covers removed. A base 20 for the apparatus consists of a vertically aligned mounting ring of a substantial and solid material such as steel. This is mounted on suitable feet 22 so as to maintain it on a secure and fixed location. This ring, in use, lies around the patient and defines the extent of the concave recess 12.

A second, rotateable, ring 24 is supported on the mounting ring 20 so as to be mutually rotateable. Thus, the second ring 24 can rotate around the patient 18. On the rotateable ring 24 are a pair of first and second mounting brackets 26, 28 located diametrically opposite each other. Each extends in a direction out of the plane of the rotateable ring 24 and provides a pivotal mounting point 30 spaced from that plane.

The line passing between the mounting points 30 of the first and second mounting brackets 26, 28 passes directly through the axis of rotation of the rotateable ring 24. This point of intersection is at the same height as a patient lying on the patient table 16.

A linear accelerator (linac) 32 is mounted on the pivotal mounting points 30 on a suitable housing 34. A motor 36 is provided to allow the linac housing 34 and thus the linac 32 to be rotated about the pivotal mounting points 30. The height of the linear accelerator 32 and its direction are set so that its beam axis passes through the point of intersection defined above.

Thus, by use of the above relations, the linear accelerator can be manipulated in two directions, being the angle at which it approaches the patient 18 and the rotational direction from which it makes this approach. These can be adjusted independently, while the geometric properties of the mounting structure mean that its beam will always pass through its point of intersection. In this way, the point of intersection can be defined and the patient located relative thereto, and the linac can be moved freely so as to direct a dose at that point of intersection.

In practice, this means that the linac can be moved continuously or stepwise so as to provide a minimal dose to areas outside the target volume and a maximum dose at the target. In this way, this apparatus can replicate the treatment profile of an LGK with the use of a single linear accelerator source. As the moving parts of the device are covered, they can be rotated at speeds up to approximately 15 rpm, which will allow the radiation source to cover the positions of all the sources of the LGK in approximately 20 seconds.

Existing linear accelerator-based devices can provide similar functionality but do so via generic robotic arms. In such devices, the precision required of the device must be imposed by accurate software and by precision measurement. In the above-described embodiment, precision is engineered into the structure and therefore arises automatically.

In addition, the general background dosage is less that that which would be encountered through the LGK, since there is only a single source. Thus, a shielding can be provided more easily and more inexpensively since only the main source needs to be shielded as opposed to the shielding of a large number of sources. This shielding is achieved by the enclosure 34, the beam stop 42 and the collimator 43 which will be formed of a material which is generally radiopaque so as to limit unnecessary exposure of staff and patients outside the device. The weight of such a reduced amount of shielding will also be significantly less.

Moreover, in comparison to the existing LGK, the use of a linear accelerator allows dynamic changes to the intensity of the beam or its temporary interruption. These changes to the beam may be programmed to occur when the beam is passing through sensitive areas. This will permit the protection of sensitive areas such as the optic nerve without having to provide selective plugs to specific sources. Moreover, it is well known that to conform to irregular distributions of pathological tissue that combinations of beams collimated to different sizes are often required. As this device only has a single source a programmable collimator such as a multileaf collimator or selection of different sized collimators can be provided. The size of the collimator can be programmed to change at certain times in the treatment. The device can also be used for imaging by suitable variation of the output energy as (for example) shown in our previous patent application WO 01/11928 or otherwise. In this way, specific areas of the patient (such as the auditory canal) or known objects such as the head frame or calibration items placed on the head frame can be located through an imaging function. This can provide a check of the positioning of the patient, or a dynamic adjustment of the patient positioning via the patient table.

Further, in the apparatus as described, the rotation speeds of the source can be varied. This allows the device to deal with biological factors such as the inhomogeneity of certain tumours in the resistance to radiation over their surface. In addition, the ability to vary the dose rate, collimation, and rotation speeds dynamically during treatment offers the ability to tailor the therapy or surgery in novel ways to achieve the maximum therapeutic benefit with the minimum side effects.

At the same time, the patient position can be adjusted via the patient positioning system 14, 16. This can be carried out dynamically during treatment, or stepwise between treatments and can be in addition or alternative to adjustment of the beam collimation. A system which combines dynamic beam collimation with dynamic patient positioning will in practice provide a powerful and flexible treatment potential.

Figure 6:
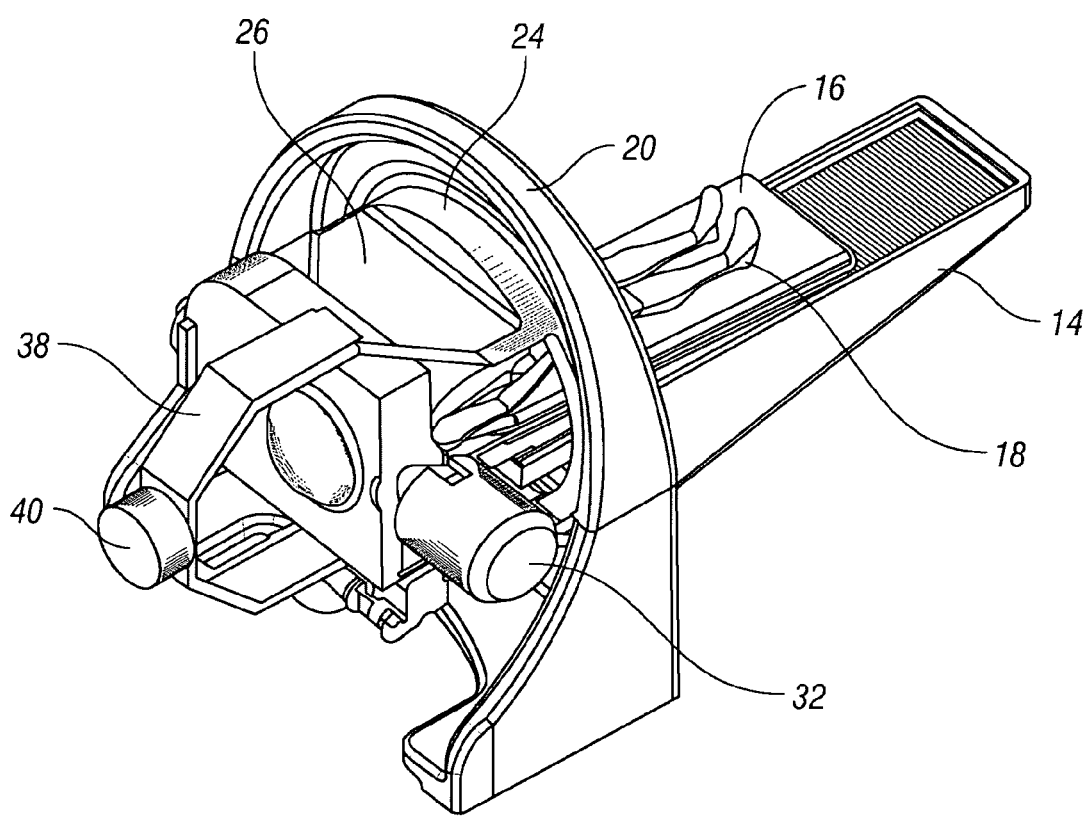
FIG. 6 shows a perspective view of the internal structure of the apparatus from a head end in a first position.
Figure 7:
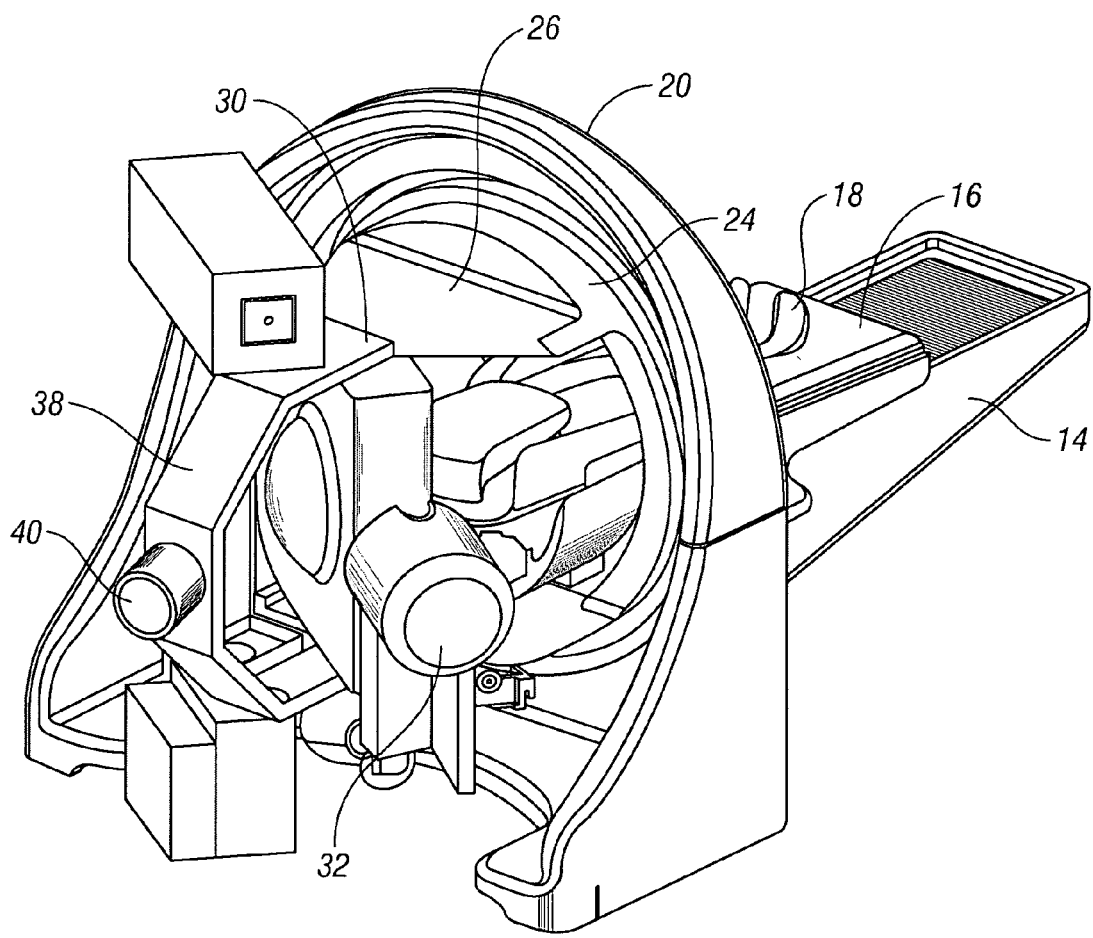
FIG. 7 shows the same apparatus in a second position.

FIG. 6 onwards show further detail of this and other embodiments. In FIG. 6 an arrangement is shown in which the mounting brackets 26, 28 are continued backwards and joined via a U-shaped link arm 38. This provides additional rigidity to the structure and enables a rotateable electrical connection 40 to be provided to bring power on to the rotateable structure. In FIG. 6, the device is shown with the pivot axis 30 vertical and the linear accelerator 32 at a low deflection of 5° relative to the patient axis. In FIG. 7, the same apparatus is shown at an increased accelerator angle of 35°.

Figure 8:
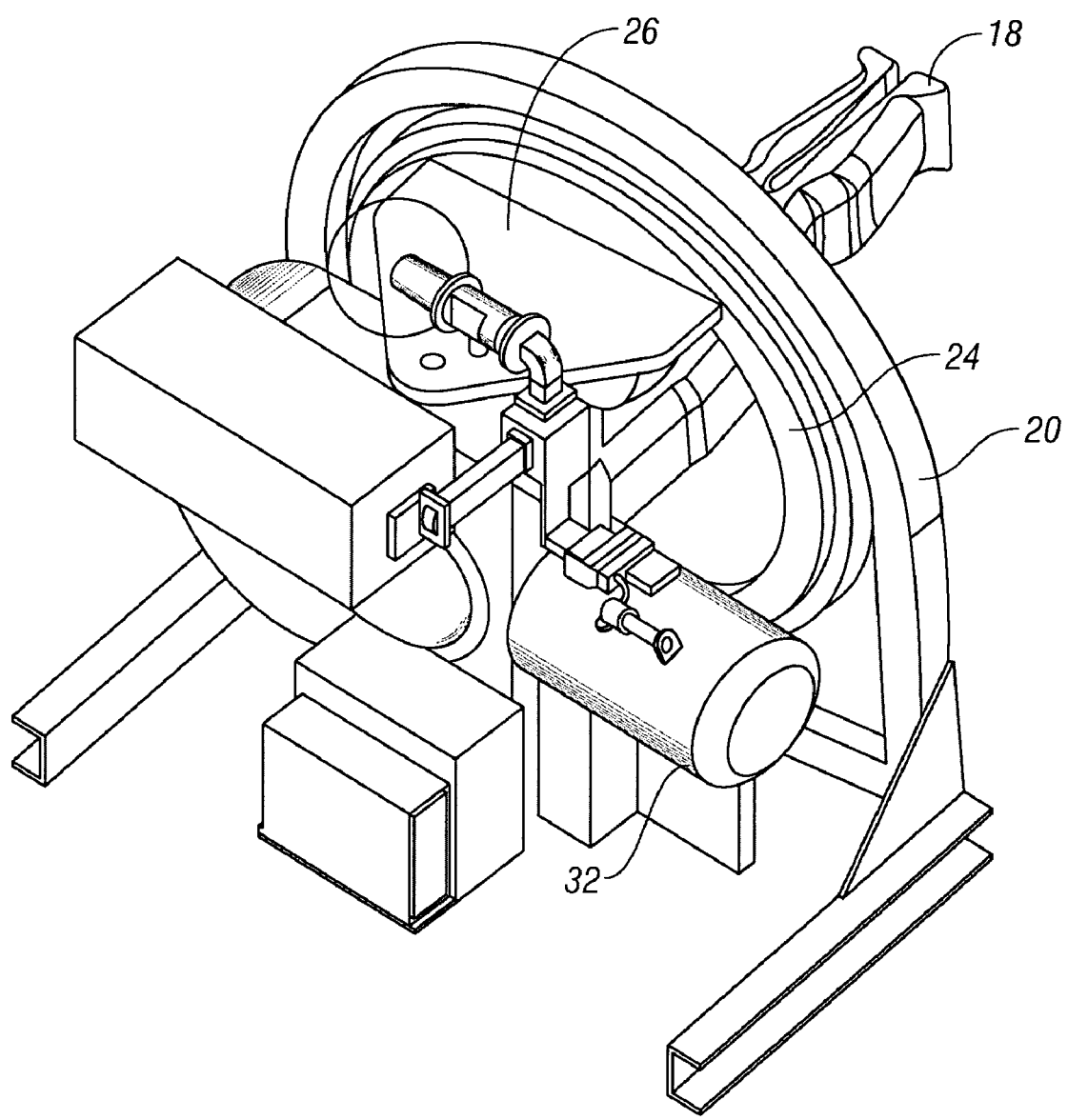
FIG. 8 shows a second embodiment of the device in a perspective view from the head end.

FIG. 8 shows the device of FIG. 5 at a low angle relative to the patient, of approximately 5°.

Figure 9:
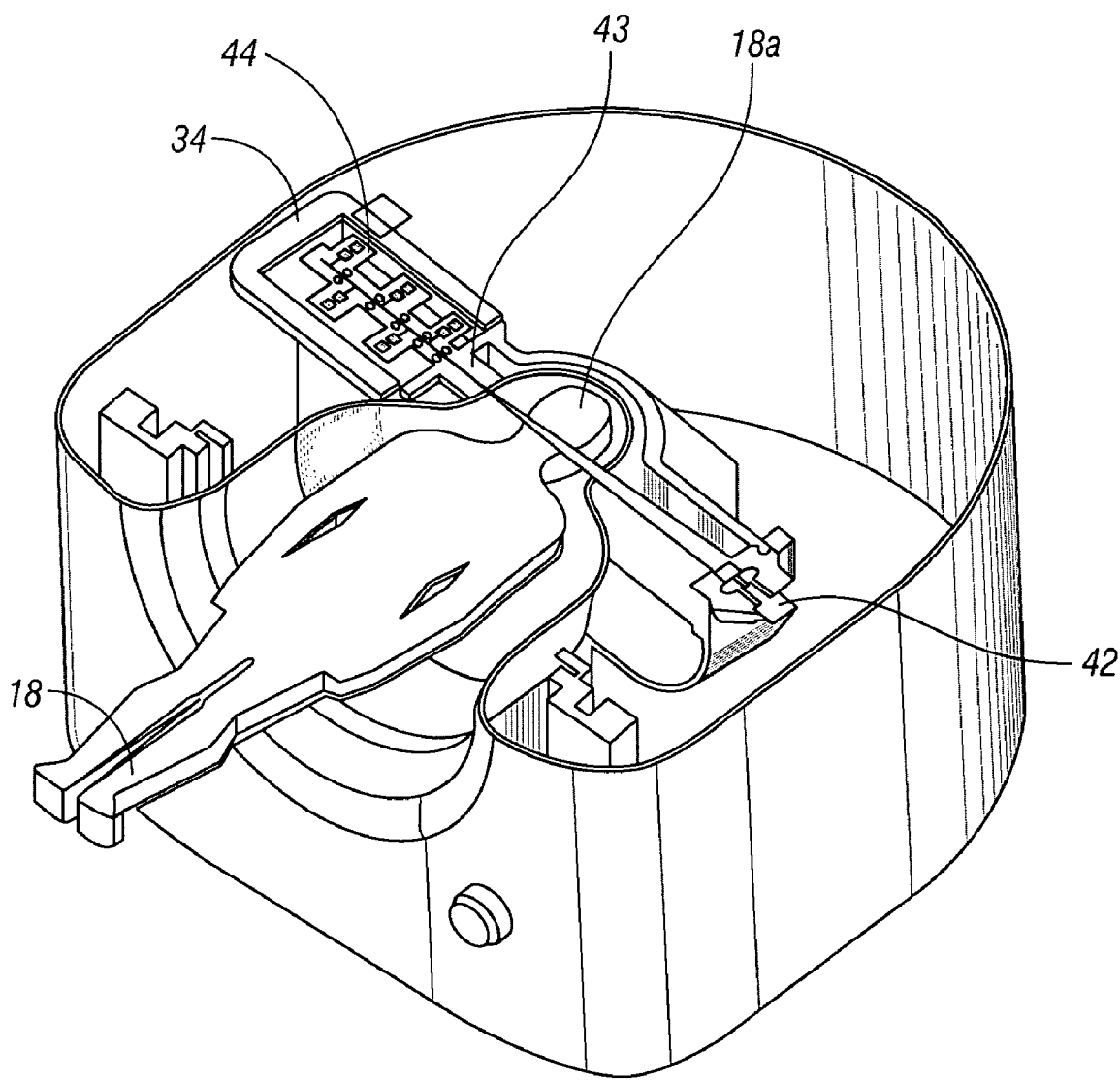
FIG. 9 shows the beam orientation in the sectional view.

FIG. 9 shows the general geometry of the device relative to the patient 18. In the arrangement shown in FIG. 9 (at 5° relative to the patient), it can be seen that there is ample space for an irradiation of the patient head 18a and that shielding 42 can be provided which will remain opposite the linear accelerator 44 and thus move with it. As a result, the shielding provided can be minimised thereby reducing the overall weight and cost of the device.

Figure 10:
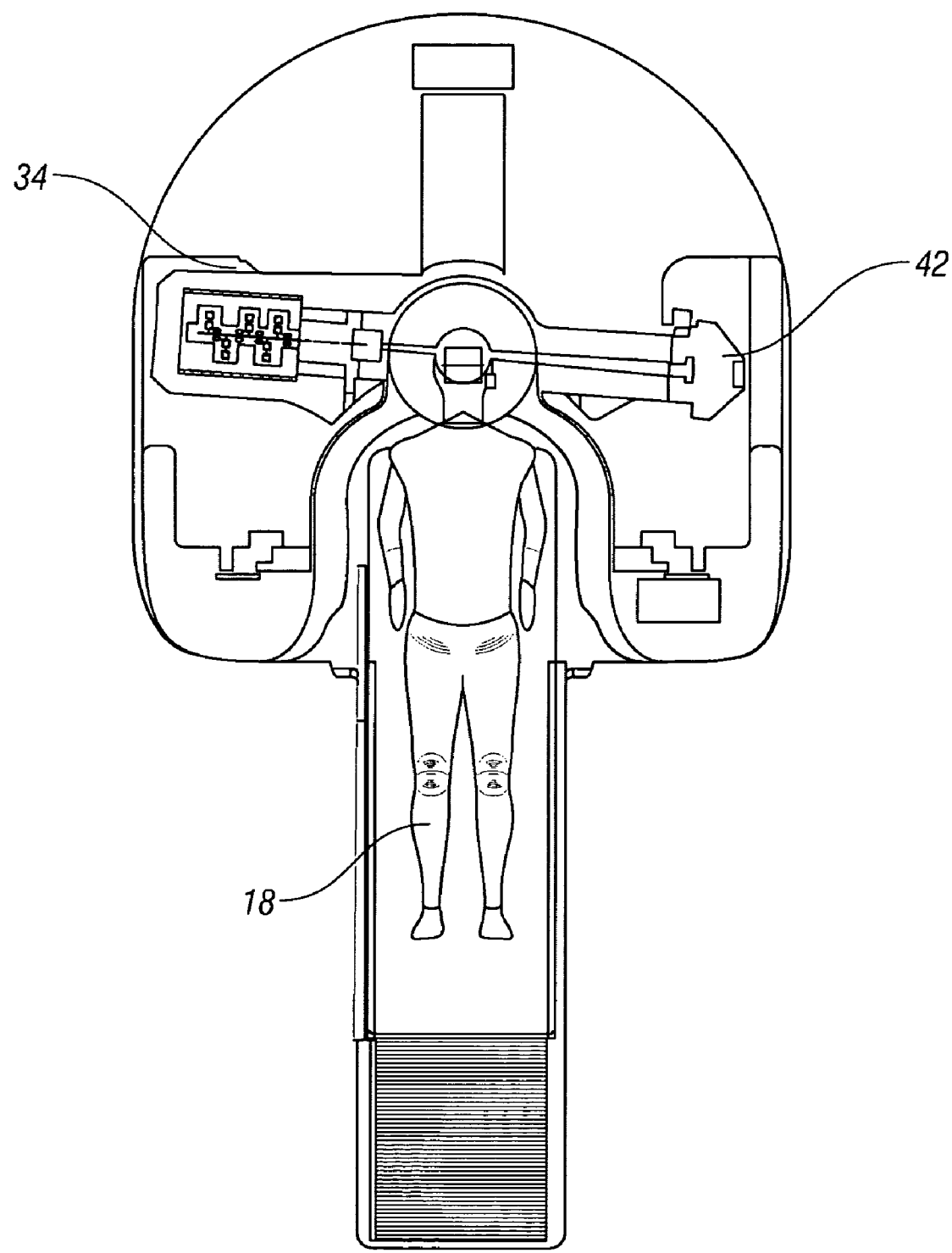
FIG. 10 shows the beam orientation of FIG. 7 in plan view.

FIG. 10 shows the same device as FIG. 9, in plan.

Figure 11:
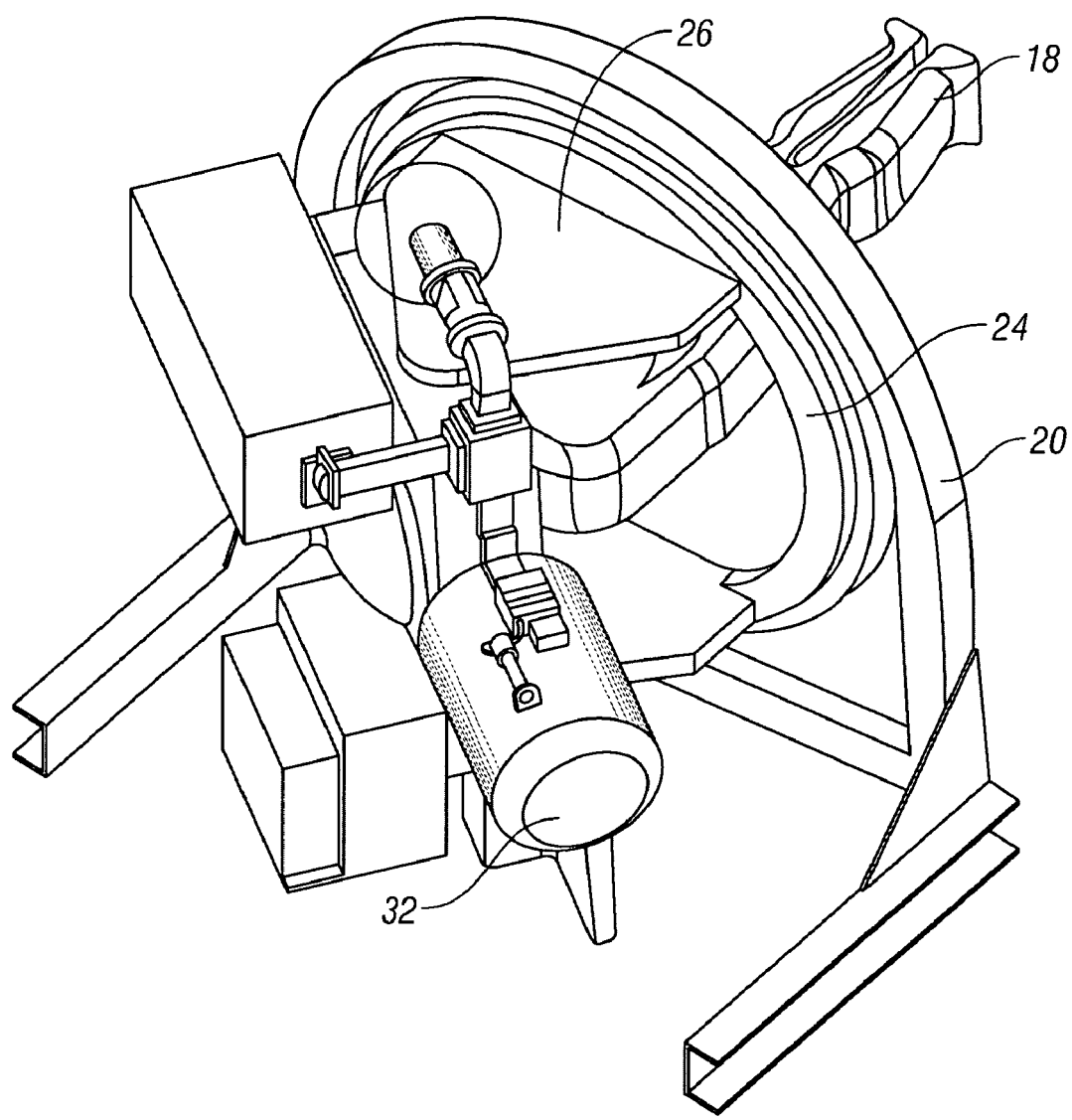
FIG. 11 shows a perspective view from the head end of the internal structure of a second embodiment in a second position.
Figure 12:
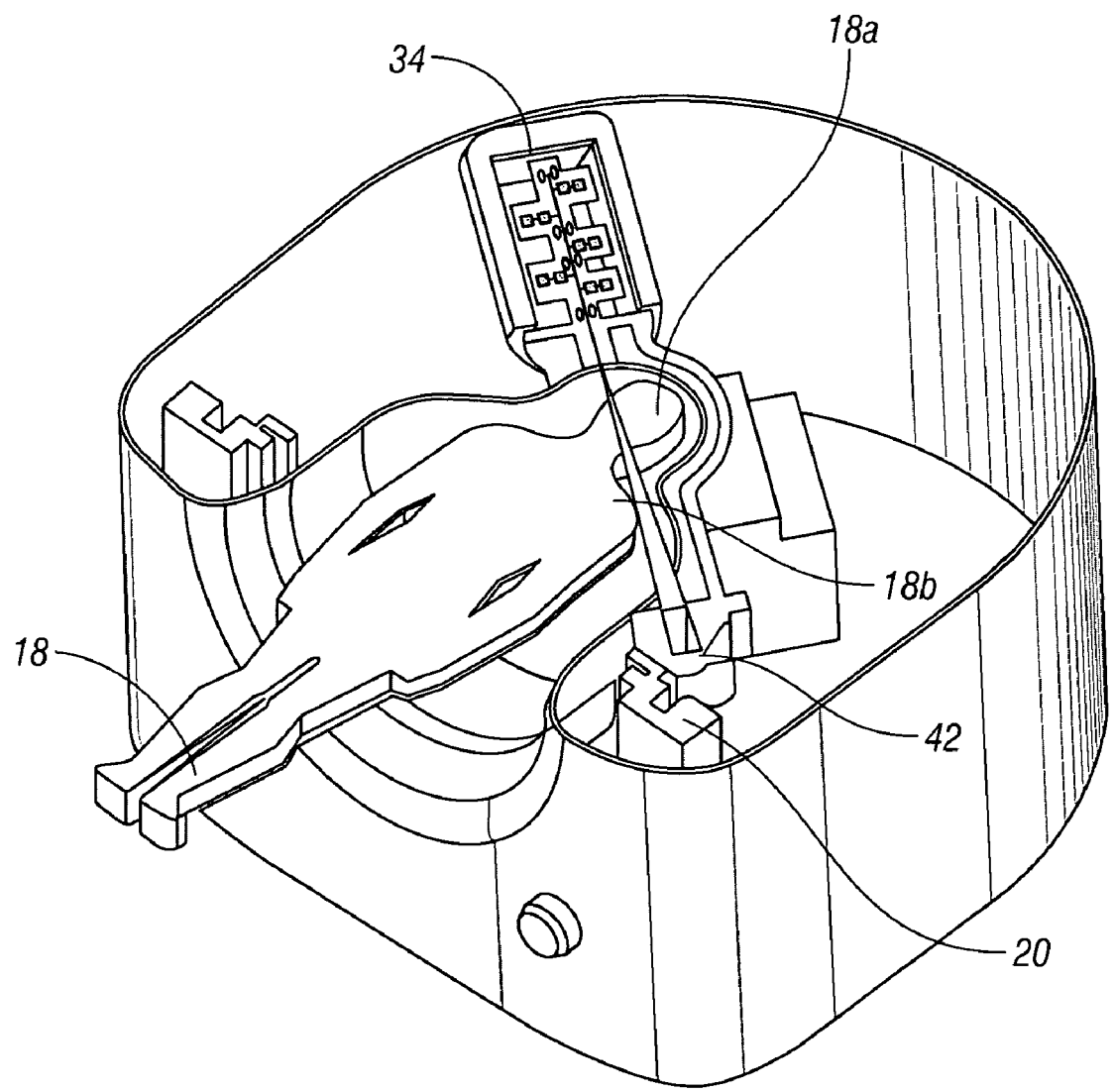
FIG. 12 shows the beam structure in this position, in a perspective view.
Figure 13:
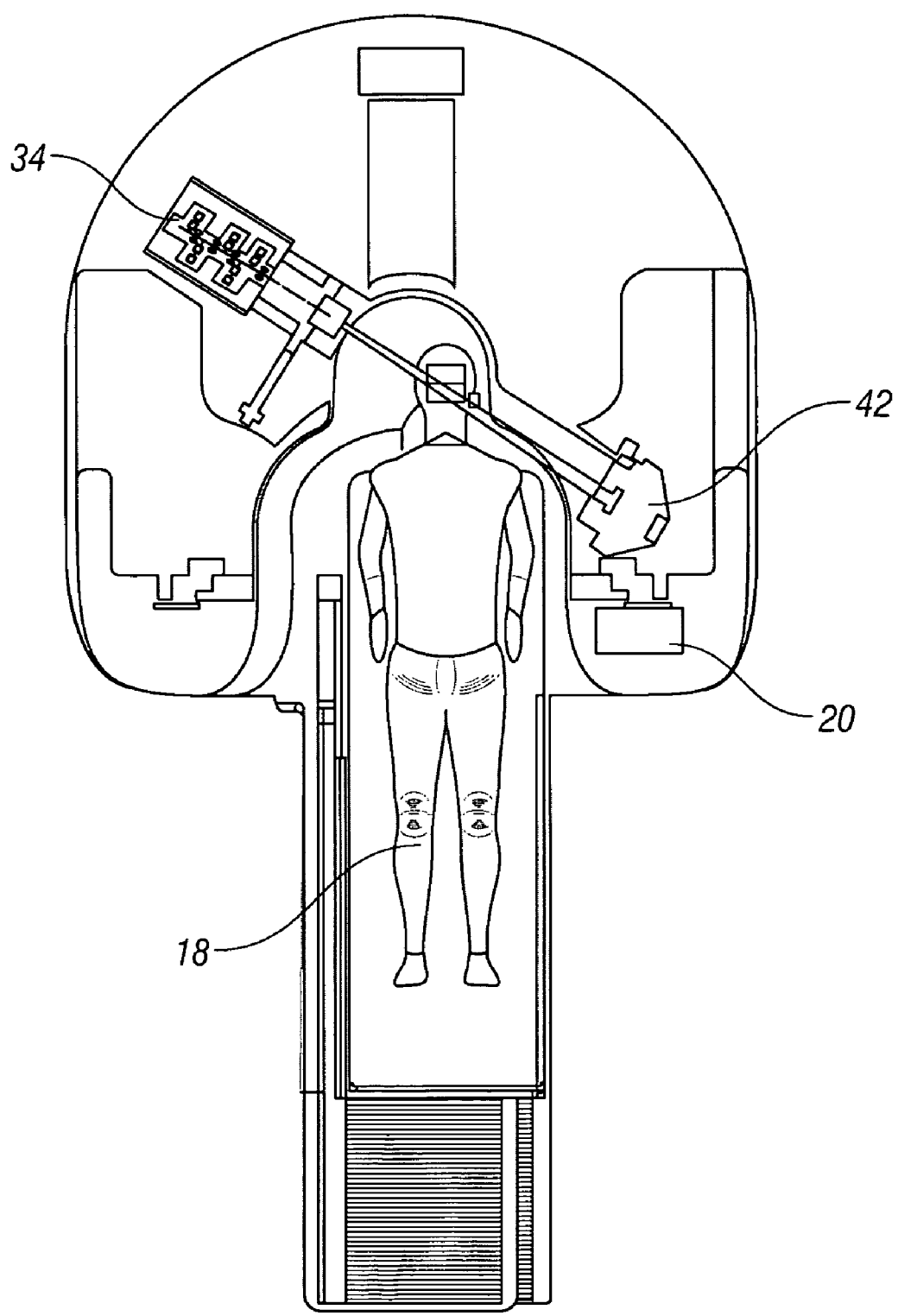
FIG. 13 shows the beam structure of FIG. 10 in plan view.

FIG. 11 shows the general arrangement as shown in FIG. 8 but with the linear accelerator at an increased angle of 35°. FIG. 12 shows the arrangement of the parts within the device at this increased angle, from which it can be seen that the angle of up to 35° can be obtained without fouling other items such as the mounting ring 20 and without irradiating unintended areas such as the patient shoulder 18b. FIG. 13 shows this arrangement in plan form.

Figure 14:
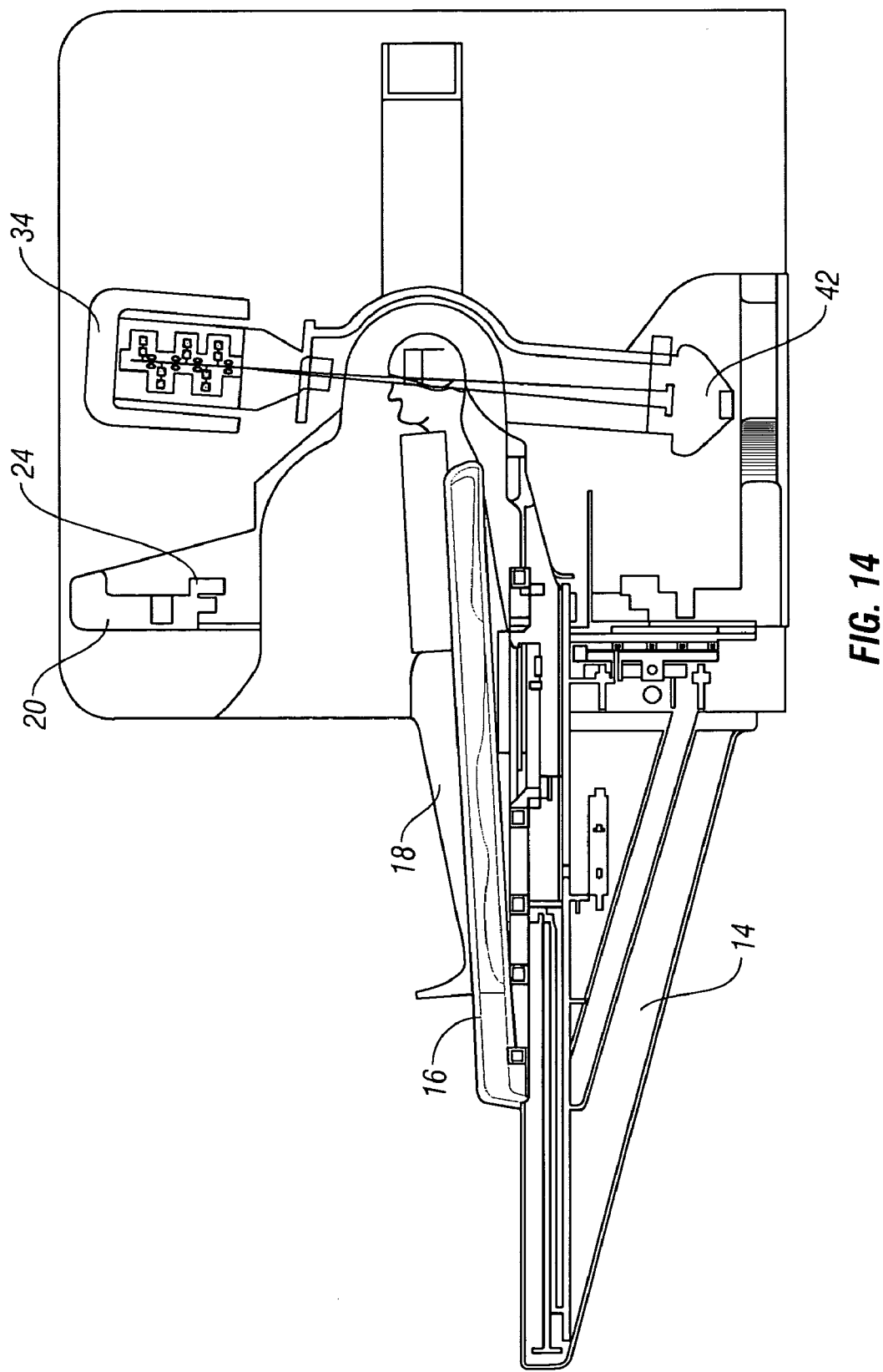
FIG. 14 shows a vertical cross section through the device in a first position.
Figure 15:
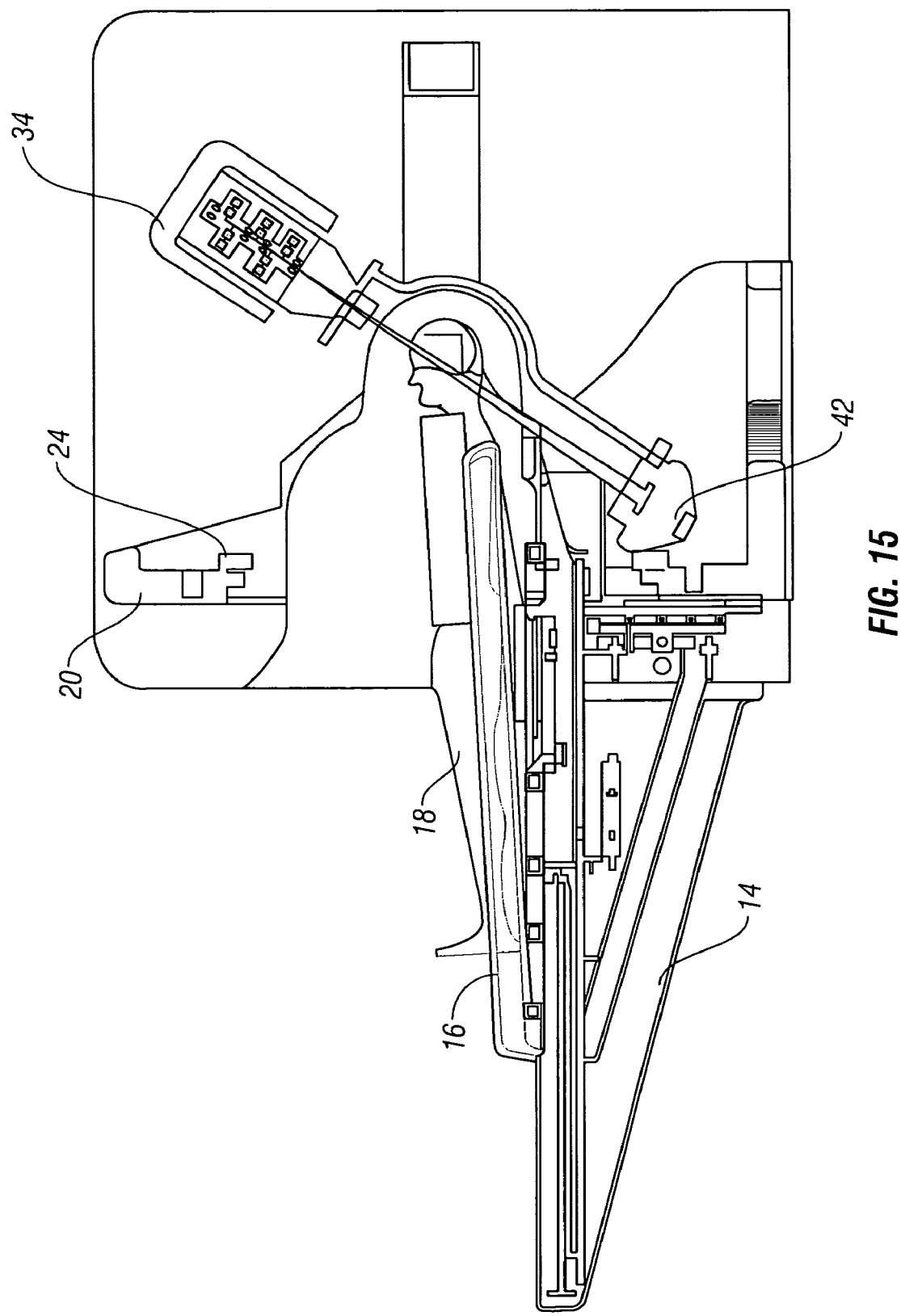
FIG. 15 shows a vertical cross section of the device in a second position.

As shown in FIGS. 14 and 15, by rotating the second (rotateable) ring 24 relative 24 to the mounting ring 20 through 90°, the linear accelerator 34 can be lifted (or lowered, not shown) into a vertical position relative to the patient and can then irradiate the relevant area of the patient from above, or indeed from any desired angle. FIG. 14 shows the linear accelerator at an angle relative to the vertical of 5° and FIG. 15 shows the same linear accelerator at an increased angle of 35°.

Figure 16:
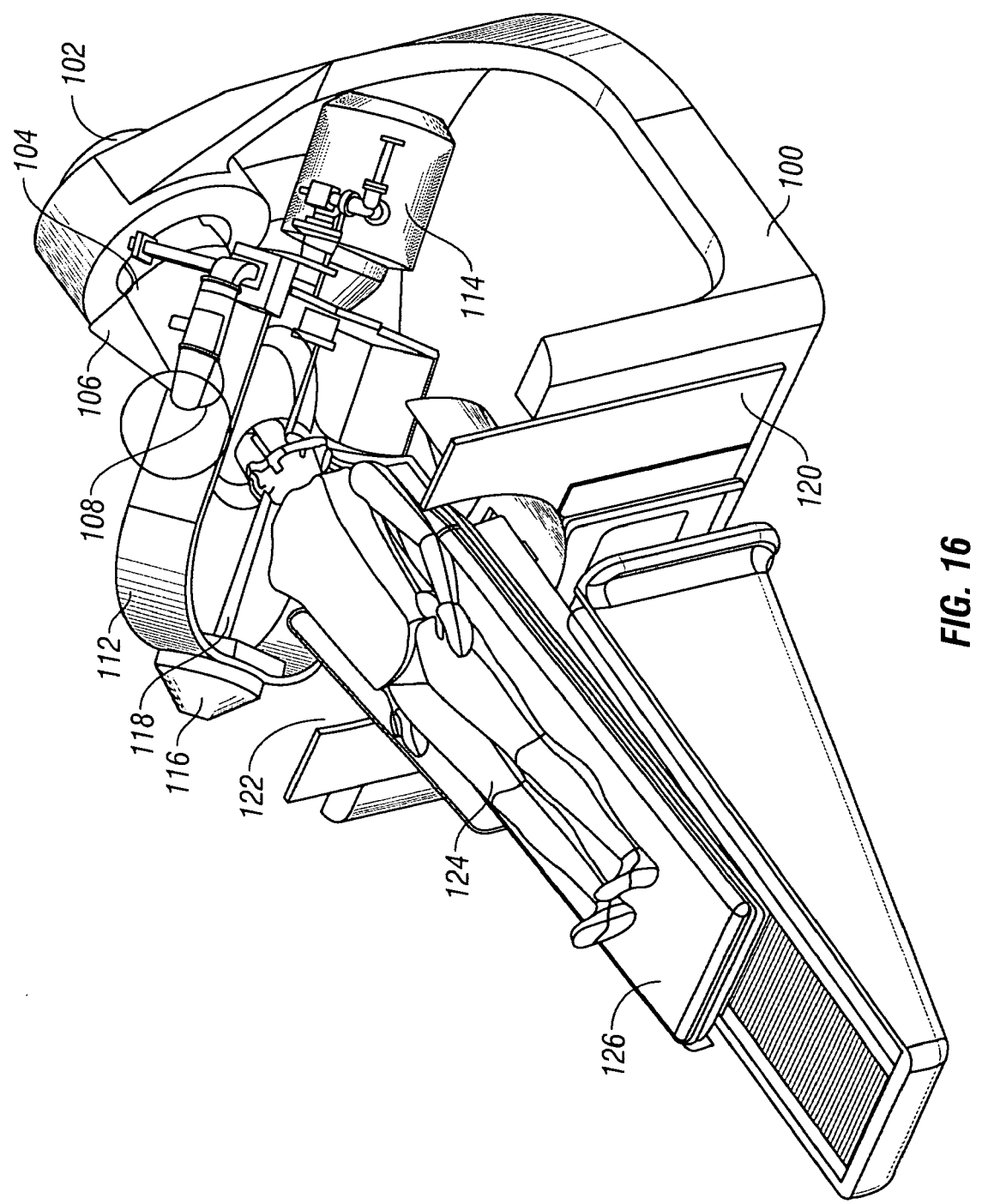
FIG. 16 shows a perspective view of a third embodiment with the radiation source in one position.
Figure 17:
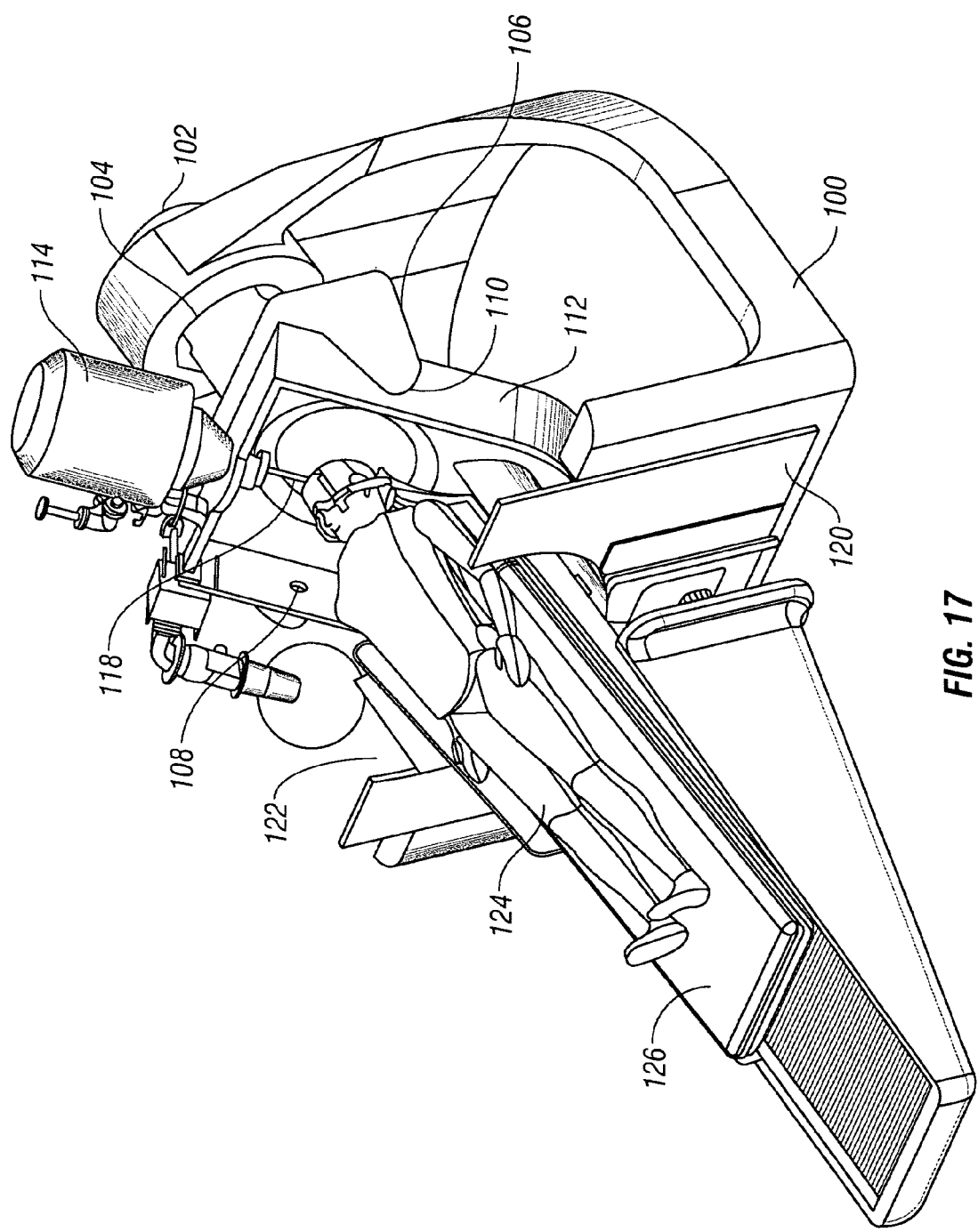
FIG. 17 shows a corresponding view of the embodiment of FIG. 14 with the radiation source in a different position.

FIGS. 16 and 17 show a third embodiment. In this alternative design, the base 100 carries a rotateable bearing 102, which supports a spindle 104 that is therefore rotateable. The spindle 104 carries a C-arm 106 at the ends of which are a pair of aligned pivots 108, 110. The pivots 108, 110 are aligned such that their shared axis is co-incident with the axis of rotation of the spindle. In this embodiment, the preferred arrangement of orthogonal co-incidence is illustrated.

A radiation source support 112 is mounted on the pivots and consists of a concave enclosure on which is provided a radiation source 114 opposite a beam stop 116. The source is adapted to produce a collimated beam 118, which passes within the concave area, through the co-incidence point of the two axes, and ends at the beam stop 116.

The entire structure is enclosed within a suitable enclosure, shown partly at 120. An aperture or recess 122 is provided in the enclosure to allow entry of a patient 124 into the concave enclosure of the radiation source support 112. In practice, the patient 124 will be supported on a moveable patient table 126 which can extend and retract the patient into and out of the concave enclosure.

This embodiment will provide the same accuracy and alignment advantages as the embodiments described above, and can be operated in substantially the same manner.

It will thus be appreciated that the present invention provides a versatile radio surgery device that is capable of precision work. It can retain both the accuracy and functionality of multiple source devices such as the LGK whilst achieving the increased flexibility and reduced weight of accelerator-based designs.

Thus, the device described provides a powerful tool in radiosurgery and radiotherapy. It is applicable both (as described) to treatment of the cranial and nearby regions, and also to other parts of the body where these are susceptible to placement within the device. It will of course be understood that many variations may be made to the above-described embodiment without departing from the scope of the present invention.

The invention claimed is:

1. A device for treating a patient with ionising radiation comprising:
   a ring-shaped support, on which is provided a mount,
   a radiation source attached to the mount;
   the support being rotateable about an axis coincident with the centre of the ring;
   the source being attached to the mount via a rotateable union having a an axis of rotation axis which is non-parallel to the support axis;
   wherein the rotation axis of the mount passes through the support axis of the support and the radiation source is collimated so as to produce a beam which passes through the co-incidence of the rotation and support axes.

2. The device for treating a patient with ionising radiation according to claim 1, in which the support is disposed in an upright disposition.

3. The device for treating a patient with ionising radiation according to claim 1, in which the support and rotation axes are transverse.

4. The device for treating a patient with ionising radiation according to claim 1, in which the mount extends transverse to the support.

5. The device for treating a patient with ionising radiation according to claim 1, in which the rotation axis of the mount is located out of a plane of the support.

6. The device for treating a patient with ionising radiation according to claim 1, in which the rotation axis of the mount is substantially perpendicular to the support axis.

7. The device for treating a patient with ionising radiation according to claim 1, in which the beam direction is perpendicular to the rotation axis of the mount.

8. The device for treating a patient with ionising radiation according to claim 1, in which the radiation source is a linear accelerator.

9. The device for treating a patient with ionising radiation according to claim 1, in which the collimation of the radiation source is adjustable.

10. The device for treating a patient with ionising radiation according to claim 1, including a control means for programmably controlling the collimation of the radiation source in a manner correlated with a movement of the radiation source.

11. The device for treating a patient with ionising radiation according to claim 1, further including a patient support.

12. The device for treating a patient with ionising radiation according to claim 11, in which a position of the patient support is adjustable.

13. The device for treating a patient with ionising radiation according to claim 10, including a patient table having a position which is adjustable under the control of the control means, the control means being adapted to adjust the position of the patient table in a manner correlated with the movement of the radiation source.

14. The device for treating a patient with ionising radiation according to claim 1, in which an intensity of the radiation source is selectable as a function of a position of the radiation source.

15. The device for treating a patient with ionising radiation according to claim 10, in which an intensity of the radiation source is selectable by the control means, the control means being adapted to adjust the intensity in a manner correlated with at least one of the movement of the radiation source, the collimation of the radiation source, and a position of a patient table.

16. The device for treating a patient with ionising radiation according to claim 10, in which at least one rotation speed of the radiation source is controllable by the control means, the control means being adapted to adjust the at least one rotation speed in a manner correlated with at least one of the movement of the radiation source, the collimation of the radiation source, and the position of a patient table.

17. The device for treating a patient with ionising radiation according to claim 1, in which an integral imaging device is used to determine a position of the patient.

18. A method of treating a patient with a source that emits a beam of radiation in a direction emanating therefrom, comprising the steps of:
   i. providing a ring-shaped support for the source, the support permitting rotation about two axes each offset from the source, with both axes and the beam direction all being co-incident at a single isocentre;
ii. positioning the patient such that a diseased area of tissue is located at the isocentre;
iii. activating the source;
iv. causing rotation of the source about the two axes to achieve a greater dosage at the isocentre than around the isocentre, wherein the rotation takes place via a rotateable union of the source to the support.

19. A method according to claim 18 in which the source is activated by removing a shutter thereby permitting the beam to escape.

20. A method according to claim 18 in which the source is de-activated when the source is in specific positions relative to the two axes.

21. A method according to claim 18 in which the two axes are perpendicular.

22. The device for treating a patient with ionising radiation according to claim 10, including a patient table having a position which is adjustable under the control of the control means, the control means being adapted to adjust the position of the patient table in a manner correlated with the collimation of the radiation source.

23. The device of claim 1 wherein the rotateable union comprises a connection allowing rotation of the source around the mount.

* * * * *

UNITED STATES PATENT AND TRADEMARK OFFICE
CERTIFICATE OF CORRECTION

PATENT NO. : 7,295,648 B2  Page 1 of 1
APPLICATION NO. : 10/971298
DATED : November 13, 2007
INVENTOR(S) : Kevin John Brown It is certified that error appears in the above-identified patent and that said Letters Patent is hereby corrected as shown below:

Page 1, Column 1, Line 73: "Elektra AB (Publ)" should be corrected to read --Elekta AB (Publ)--

Signed and Sealed this

Tenth Day of June, 2008

JON W. DUDAS
*Director of the United States Patent and Trademark Office*

(12) INTER PARTES REVIEW CERTIFICATE (3458th)
United States Patent                    (10) Number:     US 7,295,648 K1
Brown                                   (45) Certificate Issued:  Feb. 23, 2024

(54) METHOD AND APPARATUS FOR TREATMENT BY IONIZING RADIATION

(75) Inventor: Kevin John Brown

(73) Assignee: ELEKTA LIMITED

Trial Number:

IPR2019-01659 filed Sep. 27, 2019

Inter Partes Review Certificate for:

Patent No.: 7,295,648
Issued:     Nov. 13, 2007
Appl. No.:  10/971,298
Filed:      Oct. 21, 2004

The results of IPR2019-01659 are reflected in this inter partes review certificate under 35 U.S.C. 318(b).

INTER PARTES REVIEW CERTIFICATE
U.S. Patent 7,295,648 K1
Trial No. IPR2019-01659
Certificate Issued Feb. 23, 2024

AS A RESULT OF THE INTER PARTES REVIEW PROCEEDING, IT HAS BEEN DETERMINED THAT:

Claims 1-4, 7-13, 16-18, 20, 22 and 23 are cancelled.

\* \* \* \* \*